US00PP31709P3

(12) United States Plant Patent
van Langen

(10) Patent No.: US PP31,709 P3
(45) Date of Patent: Apr. 28, 2020

(54) XPACYVERIA PLANT NAMED 'TSAECH1805'

(50) Latin Name: ***Echeveria* hybrid 'Perle von Nurnberg' x *Pachypythum oviferum***
Varietal Denomination: TSAECH1805

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/501,048

(22) Filed: Feb. 13, 2019

(65) Prior Publication Data

US 2019/0281747 P1 Sep. 12, 2019

(30) Foreign Application Priority Data

Mar. 8, 2018 (QZ) ..... PBR 2018/0704

(51) Int. Cl.
*A01H 5/02* (2018.01)
*A01H 6/00* (2018.01)
*A01H 5/12* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
CPC ... A01H 5/12; A01H 5/00; A01H 5/02; A01H 6/00; A01H 6/80
See application file for complete search history.

*Primary Examiner* — Keith O. Robinson
(74) *Attorney, Agent, or Firm* — Samuel R. McCoy, Jr.

(57) ABSTRACT

A new and distinct x*Pachyveria* plant named 'TSAECH1805' which is characterized by an abundance of strong, thick succulent foliage arranged in a stemless rosette, upright juvenile foliage at the center of the rosette which becomes progressively more relaxed with age, glaucous blue-gray foliage which becomes progressively darker towards the outer whorls of the rosette, foliage which is lightly suffused and margined greyed-orange towards the apex, as well as the stability of these characteristics from generation to generation.

4 Drawing Sheets

Latin name of the genus and species: The Latin name of the genus and species of the novel variety disclosed herein is *Echeveria* hybrid 'Perle von Nurnberg' x *Pachypythum oviferum* which is also known by the nothogenus, x*Pachyveria*.

Variety denomination: The inventive variety of x*Pachyveria* disclosed herein has been given the variety denomination 'TSAECH1805'.

CROSS REFERENCE TO RELATED APPLICATIONS

This application claims priority to the Community Plant Variety Rights application number 2018/0704, filed Mar. 8, 2018, which is herein incorporated by reference.

BACKGROUND OF THE INVENTION

Parentage: 'TSAECH1805' is an intergeneric hybrid seedling selection resulting from the controlled pollination of *Echeveria* hybrid 'Perle von Nurnberg' (not patented), the seed parent, with an unnamed *Pachypythum oviferum* plant (not patented), the pollen parent. The crossing was made by the inventor in the spring of 2015 at a commercial greenhouse in Heerhugowaard, the Netherlands. In the summer of 2016, one seedling from said cross of 2015 was observed to exhibit unique growth and foliage characteristics. The seedling was isolated for further evaluation in order to confirm the distinctness and stability of the characteristics first observed. In the autumn of 2016, upon confirmation of distinctness and stability, 'TSAECH1805' was selected for commercialization.

Asexual Reproduction: Asexual reproduction of the new cultivar 'TSAECH1805', by way of rooting leaf cuttings, was first initiated in the summer of 2017 at the inventor's commercial greenhouse in Heerhugowaard, the Netherlands. Through four subsequent generations, the unique features of this cultivar have proven to be stable and true to type.

SUMMARY OF THE INVENTION

The cultivar 'TSAECH1805' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1805'. These characteristics in combination distinguish 'TSAECH1805' as a new and distinct x*Pachyveria* cultivar:

1. 'TSAECH1805' exhibits an abundance of succulent foliage arranged in a stemless rosette; and
2. 'TSAECH1805' exhibits erect foliage at the center of the rosette which becomes progressively more relaxed until the foliage at the outer whorls of the rosette is relaxed to near horizontal; and
3. 'TSAECH1805' exhibits strong, thick foliage with a narrowly obovate to obovate shape; and 4. 'TSAECH1805' exhibits moderately to heavily glaucous foliage which generally appears to be blue-gray and becoming progressively darker towards the outer whorls of foliage; and
5. 'TSAECH1805' exhibits foliage which is lightly suffused and margined greyed-orange towards the apex.

BOTANICAL DESCRIPTION OF THE PLANT

Figure 1:
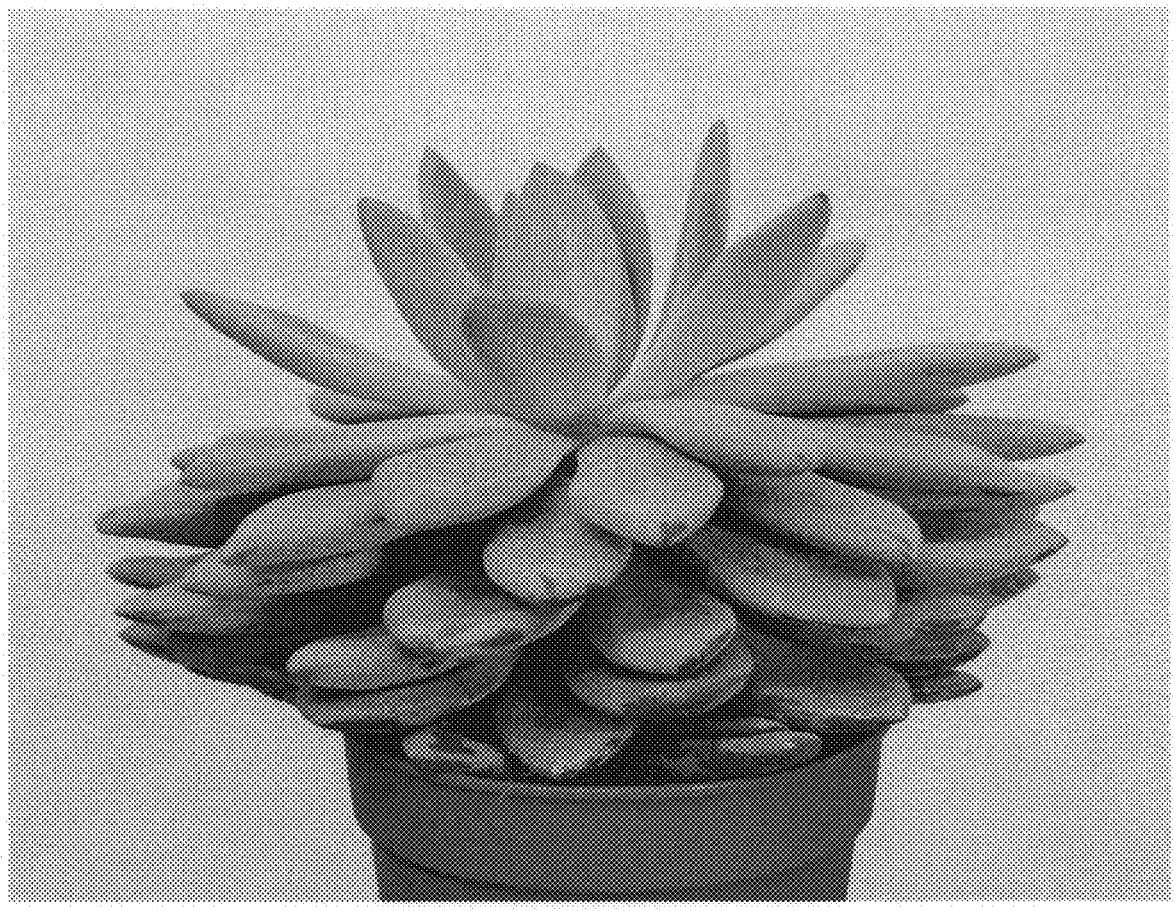
FIG. 1 illustrates, as nearly true as it is reasonably possible to make the same in color photographs of this type, an exemplary plant of 'TSAECH1805' grown in a commercial greenhouse in Heerhugowaard, the Netherlands. This plant is approximately 12 months old, shown planted in a 12.5 cm container.
Figure 2:
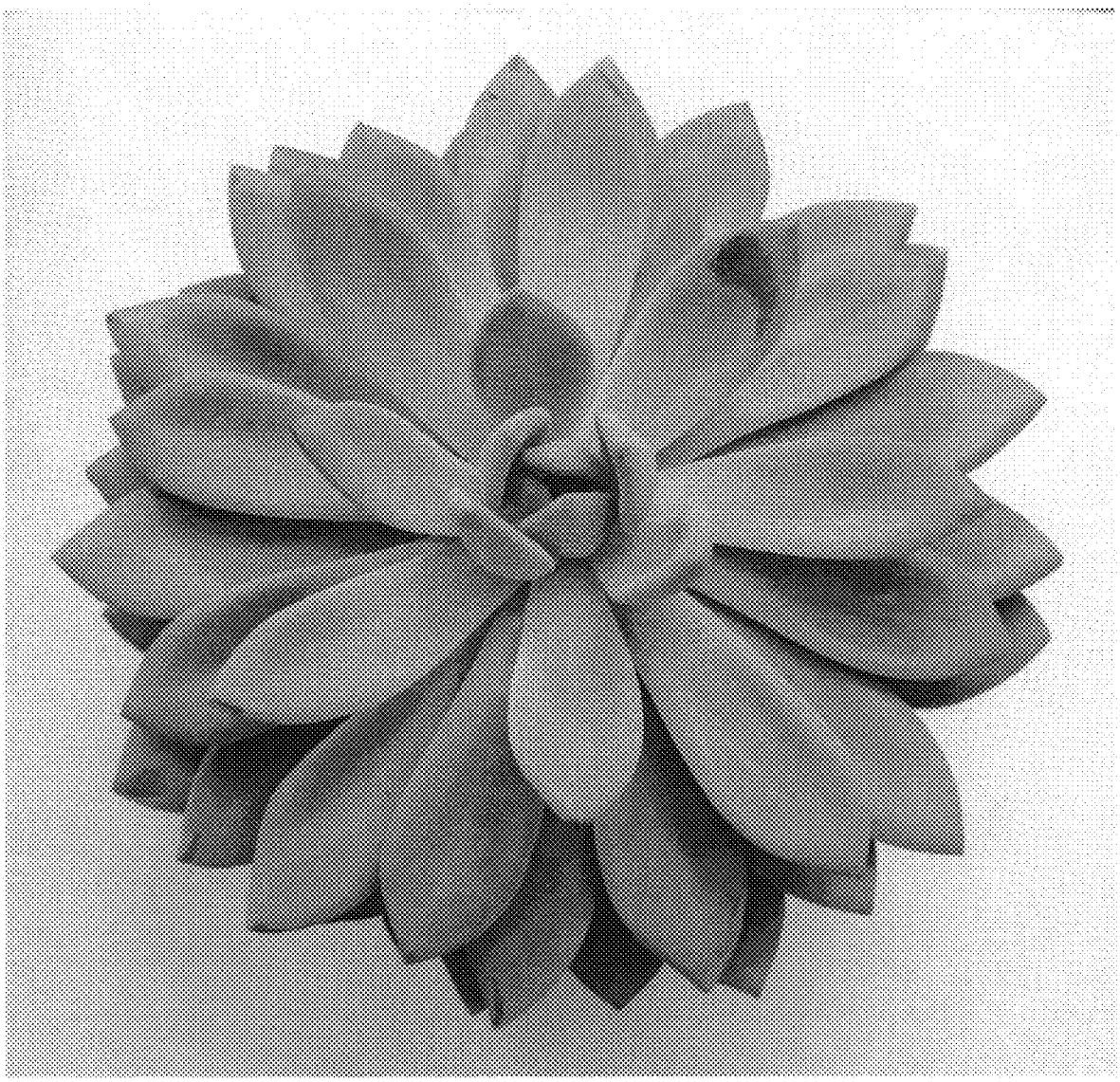
FIG. 2 illustrates, as nearly true as it is reasonably possible to make the same in color photographs of this type, the typical foliage arrangement of 'TSAECH1805'.
Figure 3:
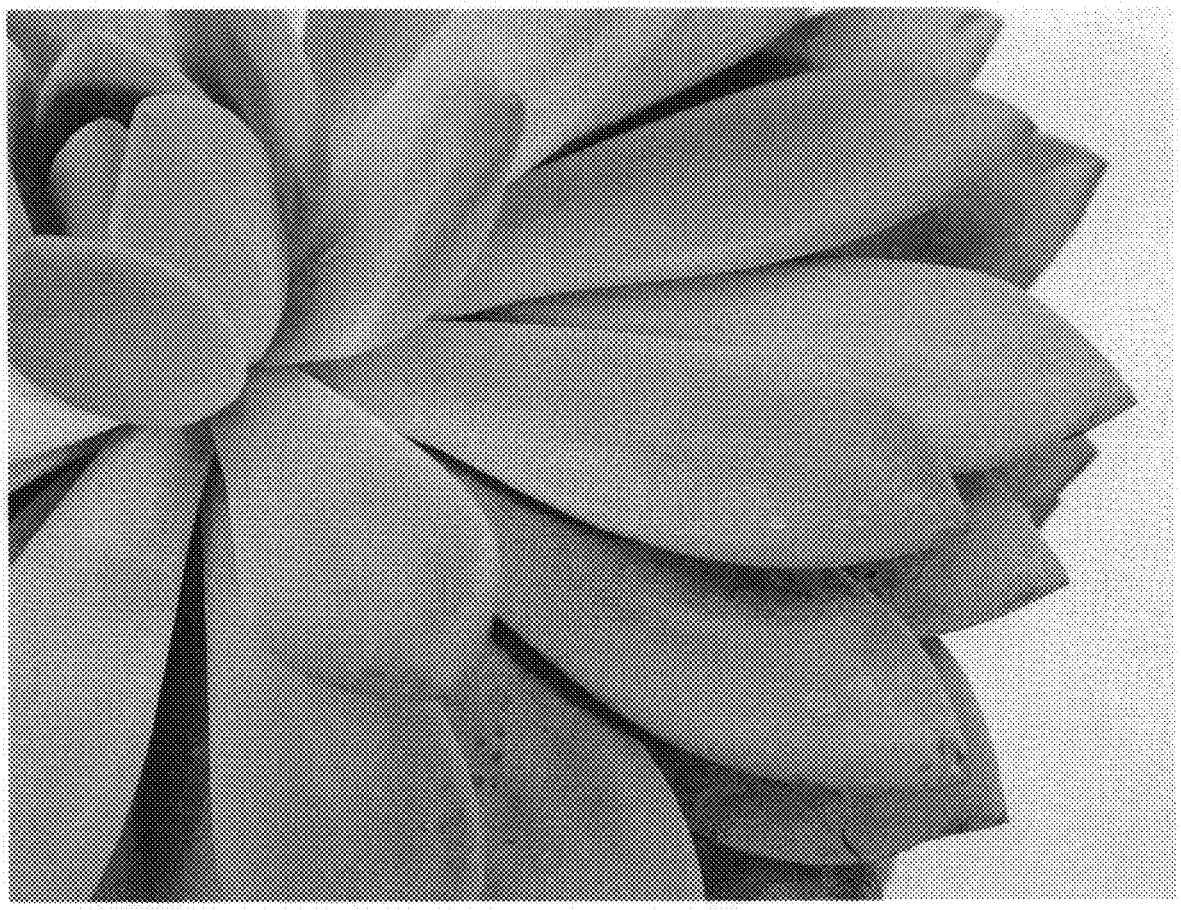
FIG. 3 illustrates, as nearly true as it is reasonably possible to make the same in color photographs of this type, the adaxial surface of the juvenile and mature foliage of 'TSAECH1805'.
Figure 4:
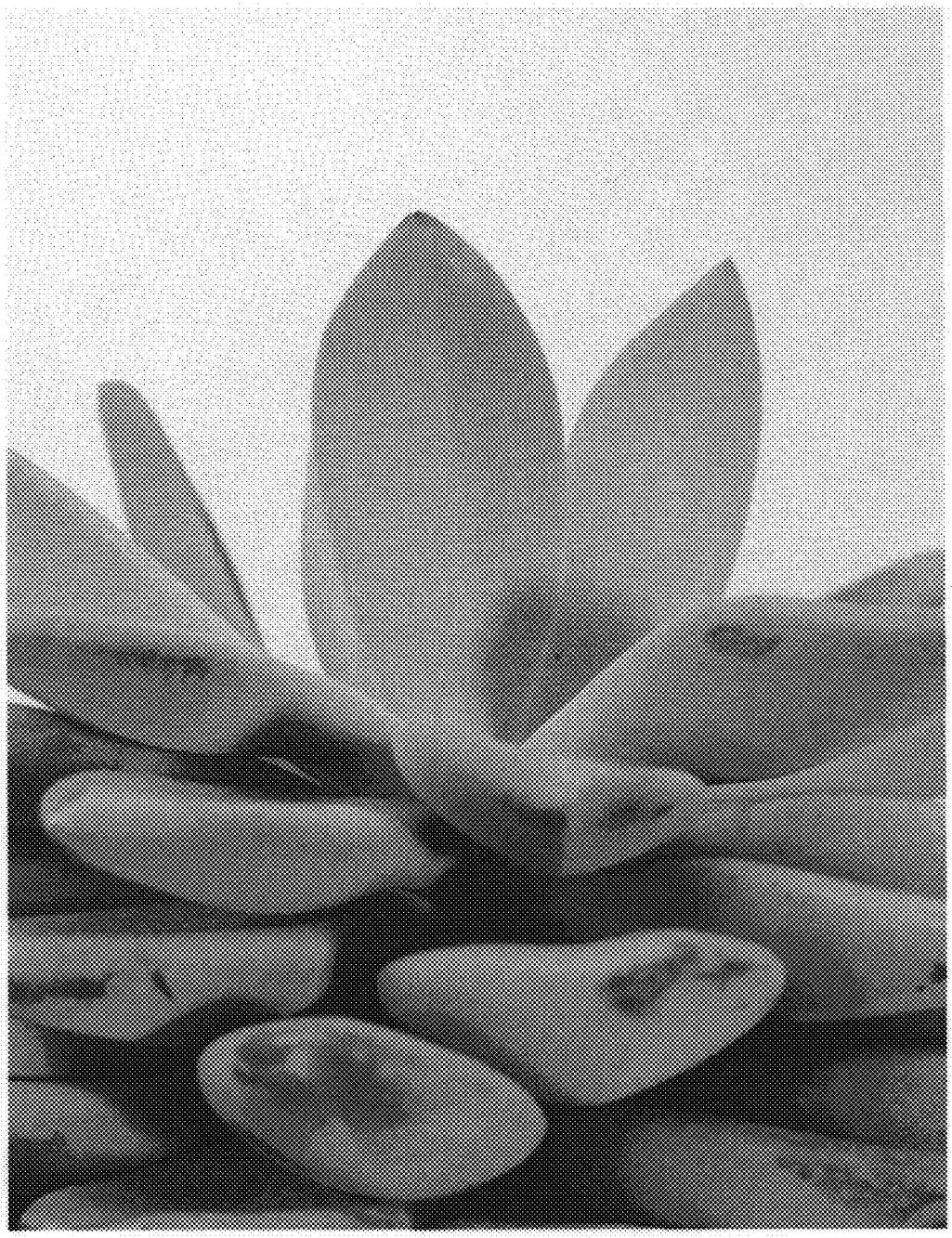
FIG. 4 illustrates, as nearly true as it is reasonably possible to make the same in color photographs of this type, the abaxial surface of the mature foliage of 'TSAECH1805'.

The following observations and measurements made in December of 2018 describe averages from a sample set of six specimens of 12 months old 'TSAECH1805' plants grown in 12.5 cm nursery containers at commercial greenhouse in Heerhugowaard, the Netherlands. Plants were produced using conventional greenhouse production protocols for *Echeveria* and *Pachyphytum* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1805' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1805' and comparisons with the parent plants and closest known comparator are provided below.

Plant description:

*Growth habit*.—Succulent perennial with foliage growing in a stemless basal rosette.

*Plant shape*.—Flattened to flattened globular.

*Height from soil level to top of foliar plane*.—11.5 cm.

*Plant spread*.—Average of 21.6 cm.

*Growth rate*.—Moderately fast growing.

*Plant vigor*.—Moderately to highly vigorous.

*Propagation*.—Type — Leaf cuttings. Time to initiate rooting — Approximately 21 days at 18 degrees Celsius. Crop time — Approximately 35 weeks to produce a marketable plant in a 12.5 cm container.

*Disease and pest resistance or susceptibility*.—Neither resistance nor susceptibility to typical *Echeveria* and *Pachyphytum* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Foliage:

*Arrangement*.—Rosette.

*Division*.—Simple.

*Attachment*.—Sessile.

*Quantity*.—Approximately 90 leaves per rosette.

*Shape*.—Narrow obovate to oblanceolate.

*Dimensions*.—9.5 cm long, 3.2 cm wide, and 0.9 cm thick, on average.

*Aspect*.—Slightly concave.

*Attitude*.—Juvenile foliage at the center of the rosette is held upright; foliage becomes progressively more relaxed with age; mature foliage is relaxed to near horizontal.

*Apex*.—Broad acute.

*Base*.—Long cuneate.

*Margin*.—Entire; not undulated or lobed.

*Pubescence, texture and luster of the adaxial surface*.—Glabrous, smooth, and matte; moderately to heavily glaucous.

*Pubescence, texture and luster of the abaxial surface*.—Glabrous, smooth, and matte; moderately to heavily glaucous.

*Color*.—Juvenile foliage, adaxial surface — Greyed-green, nearest to RHS 191A, and fading lighter towards the base, nearest to a mixture of RHS 193A and 193B; the epicuticular glaucous wax covering the leaf surface is greyed-green, nearest to in between RHS 188A and N189C. Juvenile foliage, abaxial surface — Greyed-green, nearest to a mixture of RHS 191A and 191B, and fading lighter towards the base, nearest to a mixture of RHS 193A, 193B, and 193C; the epicuticular glaucous wax covering the leaf surface is greyed-green, nearest to in between RHS 188A and N189C. Mature foliage, adaxial surface — Yellow-green, nearest to RHS 147A, and fading lighter towards the base, nearest to a mixture of RHS 146C and 146D; lightly suffused and margined greyed-orange towards the apex, nearest to RHS 176B; the epicuticular glaucous wax covering the leaf surface is greyed-green, nearest to in between RHS 188A and N189C. Mature foliage, abaxial surface — Yellow-green, nearest to RHS 148B, and fading lighter towards the base, nearest to RHS 148C; lightly suffused and margined greyed-orange towards the apex, nearest to RHS 176B; the epicuticular glaucous wax covering the leaf surface is greyed-green, nearest to in between RHS 188A and N189C.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'TSAECH1805' differ from the seed parent, *Echeveria* hybrid 'Perle von Nurnberg' (not patented), in the following characteristics described in Table 1 below.

TABLE 1

| Characteristic | 'TSAECH1805' | 'Perle von Nurnberg' |
|---|---|---|
| Foliage shape. | Narrow obovate to oblanceolate with an acute apex. | Broad obovate with an apiculate apex. |
| Foliage dimensions. | Thicker and longer than 'Perle von Nurnberg'. | Thinner and shorter than 'TSAECH1805'. |
| General coloration of the foliage. | Generally appearing to be blue-gray and becoming progressively darker towards the outer whorls of foliage; lightly suffused and margined greyed-orange towards the apex. | Red-purple at the center of the rosette and transitioning to greyed-purple towards the outer whorls. |

Plants of the new cultivar 'TSAECH1805' differ from the pollen parent, an unnamed *Pachypythum oviferum* plant (not patented), in the following characteristics described in Table 2 below.

TABLE 2

| Characteristic | 'TSAECH1805' | Pollen parent |
|---|---|---|
| Foliage shape. | Narrow obovate to oblanceolate with an acute apex. | Ovoid. |

TABLE 2-continued

| Characteristic | 'TSAECH1805' | Pollen parent |
|---|---|---|
| Foliage dimensions. | Thinner and longer than the pollen parent. | Thicker and shorter than 'TSAECH1805'. |
| Growth habit. | Stemless rosette. | Foliage born on a stem. |
| General coloration of the foliage. | Generally appearing to be blue-gray and becoming progressively darker towards the outer whorls of foliage; lightly suffused and margined greyed-orange towards the apex. | Blue. |

COMPARISONS WITH THE CLOSEST KNOWN COMPARATOR

Plants of the new cultivar 'TSAECH1805' differ from the closest known commercial comparator, the common form of x*Graptoveria* hybrid 'Opalina' (not patented), in the following characteristics described in Table 3 below.

TABLE 3

| Characteristic | 'TSAECH1805' | 'Opalina' |
|---|---|---|
| Foliage thickness. | Thicker than 'Opalina'. | Thinner than 'TSAECH1805'. |
| Foliage strength. | Stronger than 'Opalina'. | Weaker than 'TSAECH1805'. |

That which is claimed is:

1. A new and distinct variety of x*Pachyveria* plant named 'TSAECH1805', substantially as described and illustrated herein.

* * * * *